Figure 1:
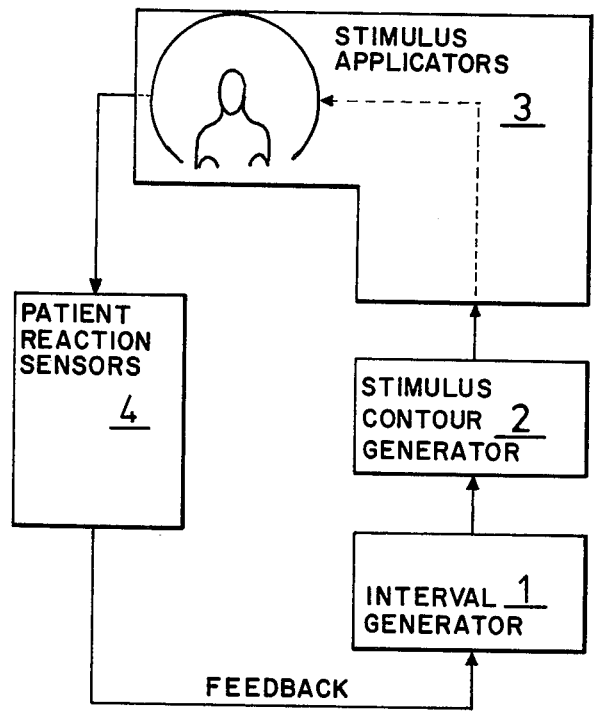

United States Patent [19]

Schweizer

[11] 4,195,626
[45] Apr. 1, 1980

[54] DEVICE FOR THE PRODUCTION AND APPLICATION OF BODY STIMULI STRUCTURES

[76] Inventor: Helgi-John Schweizer, Egerstrasse 3, 8918 Diessen, Fed. Rep. of Germany

[21] Appl. No.: 890,728

[22] Filed: Mar. 27, 1978

[30] Foreign Application Priority Data

Mar. 29, 1977 [DE] Fed. Rep. of Germany ....... 2713891

[51] Int. Cl.² .............................................. A61B 5/00
[52] U.S. Cl. ................................................... 128/774
[58] Field of Search ................. 128/1 C, 2.1 B, 2.1 R, 128/2 N, 2 R, 417, 419 R; 340/407

[56] References Cited

U.S. PATENT DOCUMENTS

| 3,014,477 | 12/1961 | Carlin | 128/1 C |
| 3,565,080 | 2/1971 | Ide et al. | 128/2.1 R |
| 3,777,938 | 12/1973 | Sugita et al. | 128/2 N |
| 3,810,457 | 5/1974 | Bottcher et al. | 128/2.1 R |
| 3,901,215 | 8/1975 | John | 128/2.1 B |

OTHER PUBLICATIONS

Goovaerts et al., "Medical and Biological Engineering", vol. 13, No. 1, Jan. 1975, pp. 112–118.

*Primary Examiner*—William E. Kamm
*Attorney, Agent, or Firm*—Ralph G. Hohenfeldt

[57] ABSTRACT

A biofeedback chamber for applying audible, visual, electrical or tactile stimuli to a subject according to a rhythmical pattern under microprocessor control. The subject's reactions are measured, analyzed and used to control the stimuli.

7 Claims, 12 Drawing Figures

DEVICE FOR THE PRODUCTION AND APPLICATION OF BODY STIMULI STRUCTURES

This invention relates to a device comprising a means for defining a sequence of stimuli, said means including stimulus generators and a control circuit for controlling said stimulus generators as a function of time, further comprising a means for applying the stimuli to a patient and further comprising a means for measuring the patient's reactions.

Arrangements of this type are already known in which the control circuit excites a light source to generate a flickering light which serves to activate the electroencephalogram (EEG). It is also known to design a device of the type cited at the outset in such a manner that weak current pulses are allowed to act directly upon the brain (see Koeppen S., *Therapiewoche* 15 (1965), page 165, for example). In yet another known arrangement of the type mentioned at the outset, the stimulus inducing means or stimulus generator is a video screen on which a signal is produced whose brightness is controlled by the intensity of the EEG signals of the patient watching the screen.

The known devices, however, are not capable of producing complex stimulus patterns in such a way that prolonged therapeutic effects or changes of consciousness can be provoked in this manner. Rhythmic signals which may possibly have been used in these devices are technically periodically occurring signal forms independent of any biologically relevant time-dependent processes, their causation and specific influenceability. The effects achieved are therefore frequently impossible to check and, in some cases, even detrimental to health. In the known devices, the timed course of the individual stimuli in a stimulus sequence cannot be influenced.

The object of the invention is therefore to provide a device in which the sequence of various stimuli intervals as well as the time-dependent course of the individual stimuli in the intervals can be freely selected and varied in a simple manner.

This object is accomplished with a device of the type mentioned at the outset in that the control circuit includes a rhythm generator adapted to define at least one succession of intervals, during each of which stimulus signals are applied, as well as a stimulus contour generator adapted to generate in said intervals a specific course of variable stimulus signals supplied by said control circuit. The separate production of an interval sequence and the timed course of the individual stimuli to be superimposed on the interval sequence facilitates the production even of complex stimulus patterns with which the existence and the time-dependent progress of neural processes as well as the organic processes associated therewith can be influenced in a controlled manner. The rhythm interval generator is preferably designed to simultaneously produce a plurality of rhythmic intervals and the stimulus contour generator is designed to introduce the courses of the control variable associated with the plurality of interval sequences into a plurality of stimulus generators which are directly or indirectly coupled to the patient. In this way it is possible to cause stimuli of various characteristics, but with a defined association to one another to affect the patient.

In accordance with an especially preferred embodiment, the interval generator and the stimulus contour generator are formed by a computer, said computer defining an interval by the number of basic time units of which it is composed and associating a value with each basic unit to produce the stimulus signal contours in the intervals in accordance with the computer program. The computer preferably includes microprocessors which have low space requirements, which have a high computing speed and which are commercially available at a low price. By providing a buffer memory for intermediately storing the intervals, i.e. numbers representing the plurality of basic units of which an interval consists, it becomes possible to determine the actual time-dependent length of an interval by means of a control oscillator which associates a certain time-dependent length with each basic unit according to its clock frequency. In addition, under certain circumstances, the intermediate storage of the interval lengths in the buffer memory makes it possible to use instead of two or more microprocessors only a single one which establishes the interval sequence and the stimulus contour in succession. This is also possible in particular because the maximum frequency of the control oscillator normally does not exceed 4 kHz in practice.

In order to be able to organize the stimuli to which the patient is subjected in dependence on his reaction to the same, means are preferably provided for feeding back the output variables from the means for measuring the reactions of the patient to the rhythm interval generator and/or the control oscillator and/or one or more stimuli generators and/or the stimulus contour generator. Since it is expedient not to feed back the measured value(s) itself (themselves), but rather a control signal analogous thereto to the rhythm generator and/or the control oscillator and/or the stimulus generator(s) and/or the stimulus contour generator, an interface circuit is preferably provided in the feedback.

In order to ensure that the patient or test subject will be subjected only to the desired stimuli, the arrangement for stimulus application preferably has an opaque, sound-insulating cupola-shaped dome which can be lowered over a chair or a couch to receive the patient. This feature by itself is regarded as an invention. The arrangement for stimulus application preferably contains one or more light sources as optical stimulus generators which project light against the dome. A flat screen is preferably provided between the light sources and the dome. In this way a constant intensity of illumination is provided in the entire visual field without any fixable contours for the patient. Furthermore, a double projection system is preferably provided as one of the stimulus generators to project patterns, the double projection system being adapted to include fisheye lenses. This double projection system makes it possible to produce patterns or other pictorial information in the entire field of vision without any reference contours.

To produce audible stimuli, loudspeakers are positioned in the dome transversely to a predetermined position of the patient as acoustical stimulus generators.

A preferred stimulus generator or applicator for obtaining mechanical stimuli includes a contact element which is secured to a ferromagnetic piston adapted to move inside a solenoid, a return spring acting against the force of the solenoid being preferably provided for the piston. In this way, the position of the piston and thus of the contact element is dependent on the flow of current through the magnet, thereby permitting a controllable contact stimulus to be achieved as well. In order to be able to produce contact stimuli of various kinds, the contact element is interchangeable.

Another preferred stimulus generator has a body contacting brush adapted to rotate electrically on a shaft, the bristles of the brush extending radially relative to the shaft. In order to be able to apply electrical stimuli through the brush as well, the bristles are expediently of metal or are metallized.

Yet another preferred stimulus generator includes a body contacting element which is rotatable about a shaft which is eccentric relative to said contact element. In an expedient embodiment, the contact element is attached to the edge of a plate which is secured at the center to the shaft of an electromotor.

An especially preferred stimulus generator has an electrode in which loose felt for absorbing liquids is provided between two plastic sheets, said one plastic sheet being traversed by filament bundles which extend into said felt and which project externally beyond said sheet. Such an electrode is flexible and good surface contact can be established with such an electrode when an electrolyte is used as the liquid. The size and configuration of the flat electrode can be easily adapted to the given circumstances. The construction of the actual contact elements as a bundle of filaments prevents the escape of liquid by virtue of the capillary effect which exists between the filaments. This system of preventing the liquid from escaping can also be improved in that the area between said plastic sheets communicates with a reservoir and equalizing container for the liquid. This precaution ensures that no liquid will escape even when the flexible electrode is situated with a very small radius of curvature with the resultant reduction in the intervening space between the plastic sheets. The filament bundles can be positioned in an especially reliable manner if they penetrate the plastic sheet twice with both of their ends lying on the external side of the penetrated plastic sheet. It is expedient to surround the filament bundles with reinforcement jackets externally relative to the penetrated plastic sheet.

Figure 2A:
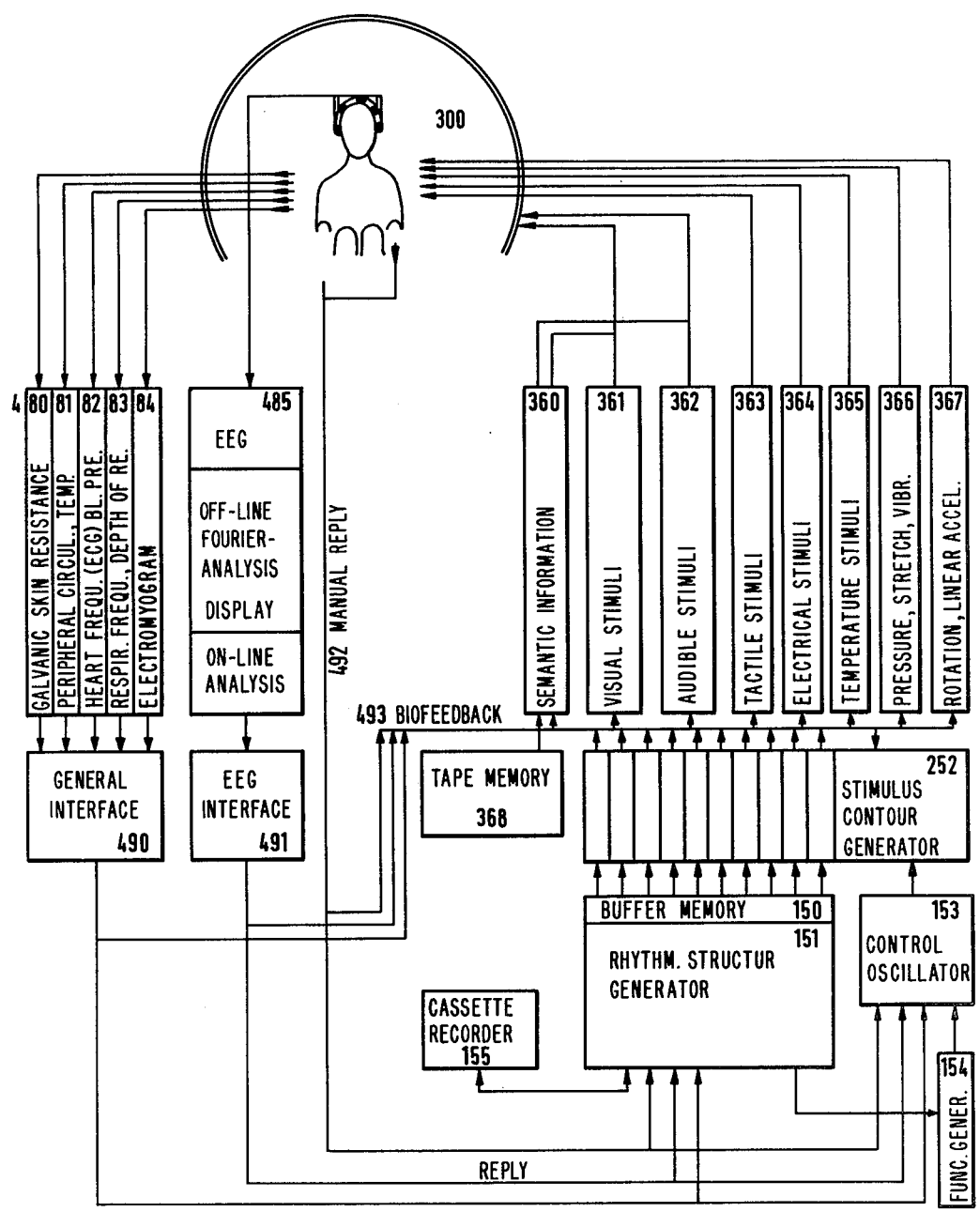
Figure 2B:
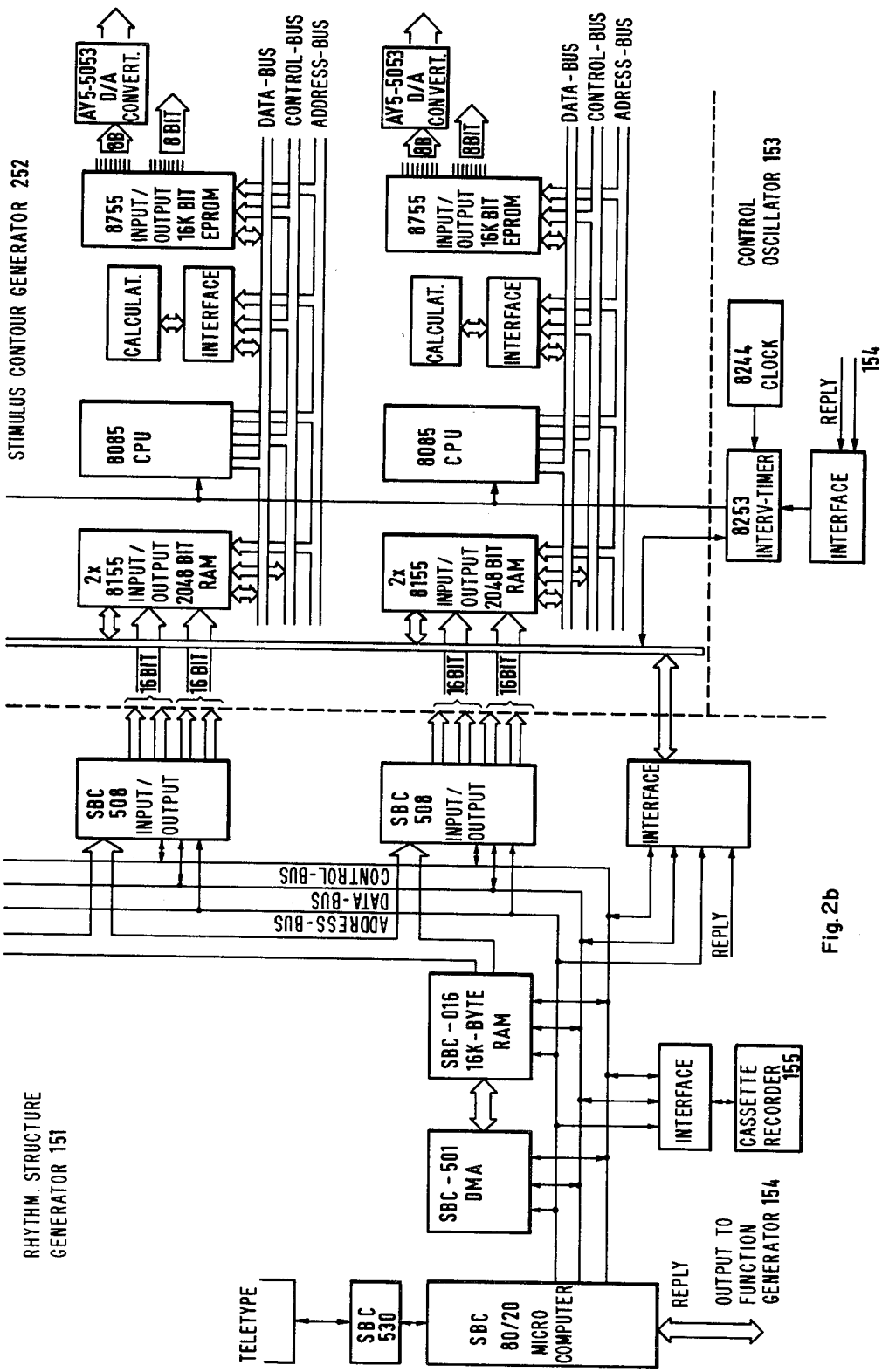
Figure 3:
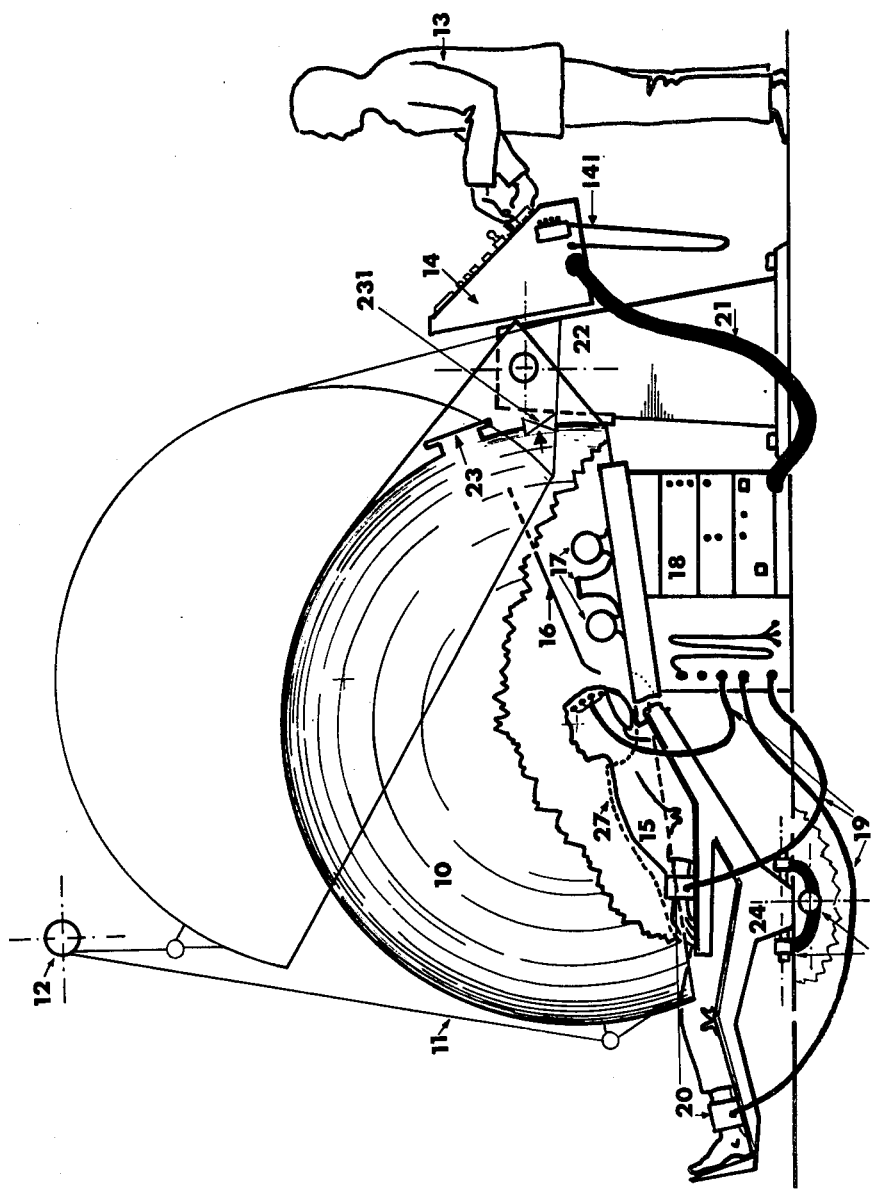
Figure 4A:
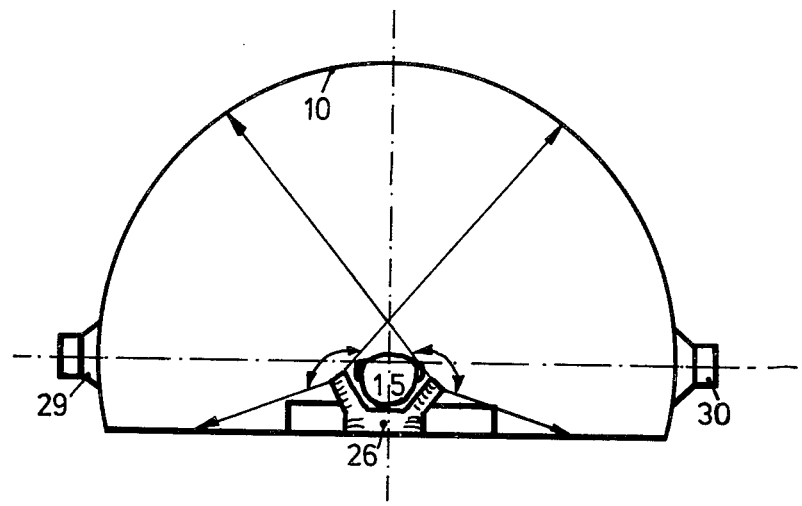
Figure 4B:
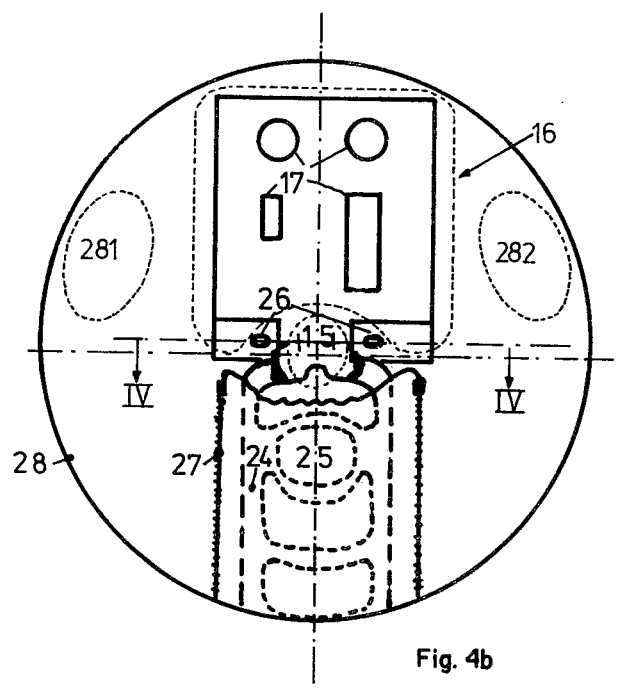
Figure 7:
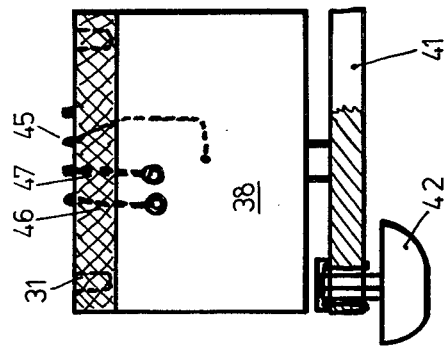
Figure 8A:
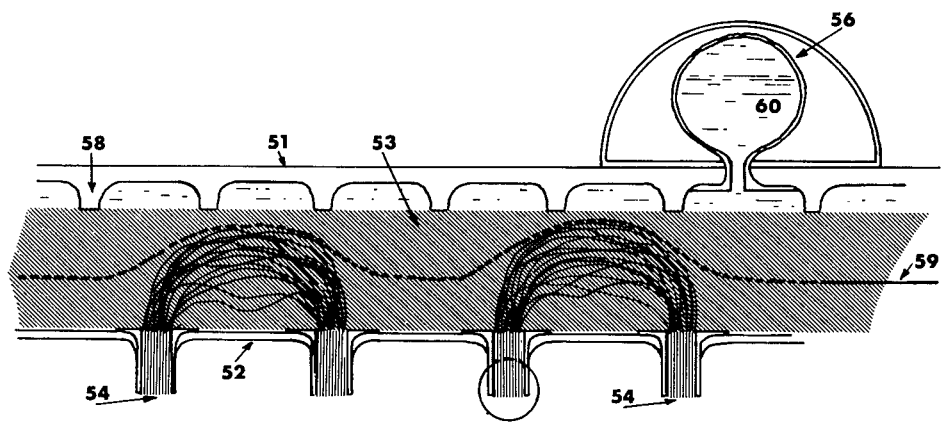
Figure 8B:
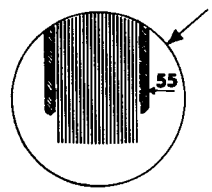
Figure 8C:

The invention will now be explained in more detail in the following with reference to preferred embodiments and in conjunction with the enclosed drawing, in which:

FIG. 1 is a principal block diagram of a preferred embodiment of a device for the production and application of rhythmic stimulus patterns in accordance with the invention, FIG. 2a is a greatly detailed block diagram of this device, FIG. 2b illustrates the rhythm generator, the stimulus contour generator and the control oscillator in the inventive device for the production and application of rhythmic stimulus patterns in a preferred structure consisting of commercially available modules, FIG. 3 is a schematic side view of the preferred embodiment of the device for the production and application of rhythmic stimulus patterns according to the invention, FIG. 4a is a section along line IV—IV in FIG. 4b, FIG. 4b is a schematic partial plan view of the device shown in FIG. 3, FIGS. 5, 6 and 7 are various stimulus generators for producing contact stimuli, FIG. 8a is a section through an electrode for use on a patient, FIG. 8b is an enlarged partial view of the end of a filament bundle of the electrode in FIG. 8a, FIG. 8c is a cross section through the end of the filament bundle from FIG. 8b to illustrate the formation of capillary zones between the filaments.

FIG. 1 shows the principal block diagram of a preferred embodiment of the device for the production and application of stimuli to a body according to the invention. Block 1 contains a rhythm interval generator which produces an interval sequence defining a rhythmic process or sequence. The output of block 1 is connected with the input of a block 2 which contains a stimulus contour generator which defines the course of the individual stimuli in the individual intervals. The output of block 2 is connected with the input of a block 3 containing stimulus generators as well as a means for applying stimuli to the test subject or the patient. The output of block 3 is connected with the input of a means depicted by block 4 for measuring the patient's reactions. A feedback of the measured results to the stimuli-producing means is provided.

FIG. 2a illustrates a more detailed block diagram of the arrangement according to FIG. 1. The block 1 in FIG. 1 contains a rhythm interval generator 151, a buffer memory 150, a control oscillator 153, a function generator 154 and a cassette recorder 155. The rhythm interval generator 151 is formed by a microprocessor with a corresponding storage capacity. The rhythm interval generator 151 operates independently (off-line) and produces the interval durations as digital values in the buffer memory 150. This means that each interval is defined by a number which constitutes the number of basic time units of which the interval is composed. These numbers are recalled by the stimulus contour generator 252 contained in block 2 in FIG. 1. The stimulus contour generator counts up to the respectively recalled number and assigns a value to each basic unit such that the series of these values arranged in succession defines the course of the stimulus or the stimulus contour in the respective interval. The speed at which the stimulus contour generator 252 counts up to the number defining the number of basic units of an interval is determined by the clock frequency of the control oscillator 153. This construction is advantageous because the stimulus contour is automatically adapted to the interval length. This approach is possible because the practical maximum clock frequency of the control oscillator which is determined by the respective use does not exceed 4 kHz so that the values for the intervals can be determined more quickly in the rhythm interval generator than they are recalled from the buffer memory 150.

The clock frequency is obtained by dividing the oscillator frequency in two programmable frequency dividers. The dividers can be set in different ways, i.e. manually or by interface circuits 490 and 491 which belong to the means for measuring the patient's reactions, or by the function generator 154, thereby permitting slow systematic changes in the basic frequency or in the entire stimulus pattern to be achieved.

The arrows between the buffer memory 150 and the stimulus contour generator 252 in FIG. 2a indicate that the rhythm interval generator 151 can simultaneously form interval sequences for a plurality of stimulus channels. The control oscillator 153 or its frequency divider can be assigned to the channels as desired.

The interval sequences for the individual channels can be freely selected within certain limits which depend on the storage capacity and computing speed of the rhythm interval generator or the microprocessors employed therein. For instance, certain stored interval series can be allowed to proceed iteratively. Several such series can follow in succession in arbitrary "group arrangements" with a defined repetition number in each case. Dead times can be established between the individual series. The individual series can be provided with a certain stochastic component (e.g. in the repetition number). The interval length can increase and decrease linearly and exponentially with selectable limit values, selectable interval number, selectable exponents and selectable time duration of intervening breaks with a constant interval length.

Furthermore, a defined dispersion of the intervals around an exact value can be introduced. This is done by adding or subtracting a random value derived from a specific theoretical probability distribution.

Furthermore, channels can be coupled for synchronization, for example for emphasis effects which require exact synchronism, and for introducing defined lead or lag times.

Furthermore, it is possible to generate random interval sequences with specific statistic parameters by previously infeeding the intervals and then recalling them randomly.

As FIG. 2a also shows, an output signal of the rhythm interval generator 151 is employed to trigger the function generator 154, thereby permitting slow changes in the clock frequency to be brought into agreement with the course of specific stimulus patterns.

The program input for the rhythm interval generator 151 and the stimulus contour generator 252 is effected through the cassette recorder 155. This can also be used as well to store the calculated rhythmic sequences. An input keyboard (not shown) can also be provided in addition to or in place of said cassette recorder 155.

The values calculated by the stimulus contour generator 252 for the basic units of the individual intervals serve as control variables for the stimulus generator or applicator which is coupled to the body. The stimulus contour generator also determines the relative duration of the dead time, i.e. the duration of the stimulus variable 0 between two stimulus events.

The actual duration of both the dead time as well as of the contour course is determined by the control oscillator 153 as already mentioned above.

The stimulus contours to be selected by the program are chosen according to physiological considerations. The contours available include, for example, rectangular or square shapes, ramp shapes, general triangular shapes, exponential functions and exponential increases and decreases with an inserted plateau.

It is possible to also employ conventional analog contour generators for a few channels in order to relieve the work-load on the stimulus contour generator assembled from microprocessors.

A preferred interval of the rhythm structure generator 151, the stimulus contour generator 252 and the control oscillator 153 assembled from commercially available modular elements is illustrated in FIG. 2b.

The central module of the rhythm interval generator 151 is a microcomputer, model SBC 80/20, manufactured by the Intel Corporation. This is connected via address, data and control busses with a SBC-016 module, a SBC-501 module and several SBC-508 modules respectively, all of which are also manufactured by Intel Corporation.

The SBC-016 component is a 16 K byte random access memory for receiving programs and prefabricated stimulus interval data from a tape cassette of the cassette recorder 155 which is also connected with the busses through an interface.

The SBC-501 component is a control unit for a direct memory access to raise the transfer rate or the transfer speed between the memory and the SBC-508 components which are the input and output modules for establishing and reproducing the 16 bit interval length values for two respective stimulus channels. Two SBC-508 components are illustrated in FIG. 2b, but their actual number is dependent on the number of stimulus channels provided. 5 SBC-508 input and output modules are provided for 10 stimulus channels.

In the stimulus contour generator 252, each SBC-508 module is associated with a component group consisting of the following components: (two) Intel 8155, 8085 CPU, Intel 8755 (all manufactured by the Intel Corporation) and a calculator, which are respectively interconnected through address, data and control busses. The calculator is connected to the busses through an interface.

The Intel 8155 component constitutes a 2048 bit static MOS random access memory with two programmable 8 bit input/output (I/O) ports. The Intel 8755 component is a 16,384 bit electrically programmable read-only memory (EPROM) also comprising two 8 bit I/O ports. The calculator module serves for acceleration and can be selected in any suitable way. For instance, the MM 57 109 component from National Semiconductor can be used.

The A Y 5-50 53 component from General Instruments is connected as a digital-analog converter downstream of one port of each Intel 8755 EPROM component.

The afore-mentioned component groups are coordinated with one another by a cross connection bus. An interface is provided for the coordination between the rhythm interval generator 151 and the stimulus contour generator 252. The feedback of measured values obtained from the patient to the rhythm interval generator 151 is introduced into said interface, too.

The control oscillator 153 includes the Intel 8253 and Intel 8224 components, both of which are manufactured by Intel Corporation. The Intel 8224 component is a clock generator. The Intel 8253 component is a programmable frequency divider which divides the frequency supplied by the clock generator and whose output is connected with the 8085 CPU components. The frequency divider is programmed through an interface to which the function generator 154 and the feedback leads for the feedback of the measured results obtained from the patient are connected on the input side.

In the embodiment according to FIG. 2b, the buffer memory 150 is integrated into the rhythm interval generator 151 and the stimulus contour generator 252. It is built by storage locations of the Intel 8155 and SBC-508 components.

A stimulus generator and applicator for visual stimuli 361, a stimulus generator for audible stimuli 362, a stimulus generator for tactile stimuli 363, a stimulus generator for electrical stimuli 364, a stimulus generator for temperature stimuli 365, a stimulus generator for pressure, stretch and vibration 366 and a stimulus generator for rotation and linear acceleration 367 are provided as stimulus generators which are connected through leads with the stimulus contour generator 252. Details of such stimulus generators are described in conjunction with FIGS. 3-8c. In addition, a generator for semantic information is also provided. The semantic information is applied through the acoustical and visual stimulus channel. The semantic information to be communicated is stored on a magnetic tape of a tape memory 368. The operation of the magnetic tape is synchronized with the stimulus contour generator, for instance by means of a stepping motor. One track of the magnetic tape regulates the intensity of the non-semantic acoustical or optical channel. The intensity of the semantic signal can be influenced by the stimulus contour generator. Examples of semantic information are music, therapeutic instructions, suggestive messages, emotional utterances in the audible range and image projections and meaningful progressions of movements in the optical range.

The individual stimuli are presented to the patient in a means for stimulus application 300. Further details of this means are described in particular in conjunction with FIGS. 3 to 4b.

The means for measuring the patient's reactions to the stimuli includes a means for measuring the galvanic skin resistance 480, a means for measuring the peripheral circulation and the peripheral temperature 481, a means for measuring the heart frequency (electrocardiogram) and the blood pressure 482, a means for measuring and respiratory frequency and depth of respiration 483, a means for measuring the electromyogram 484 and a means for measuring the electroencephalogram 485.

The means for measuring the galvanic skin resistance 480 includes surface electrodes which are positioned on the patient's body. The measurement of the peripheral circulation is performed with transmitted light photometry which can be carried out on one of the patient's fingers. A thermistor is provided for measuring the skin temperature. The means for measuring the cardiac frequency 482 includes an electrocardiograph, the electrical heart activity being registered using extremity leads with surface electrodes. The duration between two R peaks of the electrocardiogram (ECG) is measured using an interval counter. The means for measuring the respiratory frequency and the depth of respiration 483 includes thermistors which may be placed in front of the patient's mouth and nose. The evaluation of the temperature curve provides information about the respiratory frequency, the duration of inhalation and the speed of the breath. The means for measuring the electromyogram 484 also includes surface electrodes which are positioned on the patient's body. They conduct the potentials of muscular contraction of especially interesting muscles or groups of muscles in the patient. They provide information about the respective state of muscular contraction (muscular tonus).

The electroencephalogram is registered using conventional methods in the means 485 and is subjected to spectral analysis, whereby the analysis can be carried out off-line or on-line. On-line analysis is necessary if, as shown in FIG. 2, the stimulus pattern is to be influenced by the feedback of the results of analysis. The feedback occurs through an EEG interface 491 which directly generates a control signal whichis reversible for the rhythm interval generator 151 and/or the control oscillator 153 and/or the stimulus contour generator 252 and/or the body-coupled stimulus generators. The EEG interface circuit controls the rhythm interval generator, the control oscillator and the stimulus generators directly according to the frequency, phase and amplitude of the registered EEG component.

The feedback of the measured results from means 480 to 484 is effected through a general interface circuit 490 which directly generates a control signal analogous to the measurement value for the rhythm interval generator 151, the control oscillator 153, the stimulus contour generator 252 and/or the stimulus generators. The functional relation between a sliding mean value (variable width) of the measurement variable and the control signal is linear, exponential or logarithmic as desired.

The direct transfer of a measurement value from the output of the general interface circuit 490 and the EEC interface circuit 491 to a stimulus channel with the intention of consciously making perceptible an organic process which is otherwise not or only hardly observable constitutes what is conventional so-called biofeedback.

Biofeedback and the application of rhythmic stimulus patterns can progress simultaneously in a complementary way. This is done such that either the biofeedback signal is switched to control a non-rhythmic stimulus channel or a non-rhythmic stimulus variable or it is switched so that the output signal of the stimulus contour generator 252 for a certain stimulus channel is provided with a dc component and/or an amplification factor analogous to the measured body reaction. In this way an interaction of the direct effect of a stimulus and a consciously intended change of state can be achieved which is desirable for therapeutic purposes.

Moreover, a means for manual feedback 492 is also provided with which the patient can actively participate in the stimulus treatment and communicate subjective processes and conditions. Further details of means 492 will be explained and described in conjunction with FIG. 3. FIG. 3 illustrates in a schematic side view the mechanical structure of the preferred embodiment of the device for the production and application of stimulus patterns in accordance with the invention. In accordance with this embodiment, a chair 24 is provided in which the patient 15 lies in a slightly inclined position. A cupola-shaped dome 10 can be lowered over the chair 24 so that, when lowered, the center of the dome is situated approximately in the area of the root of the nose of a patient 15 lying on the chair 24. When lowered, the dome 10 is closed off at the bottom by a base plate 28 (FIG. 4) which has a recess through which the head and a portion of the trunk of the patient 15 project who is lying on the chair 24. In order to cover the patient toward the inside of said dome, a cover 27 (FIG. 4) is provided which is adapted to be attached to the edges of said recess.

In back of the area where the patient's head is located, light sources 17 are positioned which belong to the equipment for producing visual stimuli 361 and which are shielded with respect to the dome by means of a flat opaque screen 16.

The inner wall of the dome 10 and of the base plate 28, the upper side of the cover 27 as well as both sides of the flat screen 16, the sides of an equipment support 18 facing the interior of the dome 10 on which the light sources 17 are positioned, as well as all parts projecting into the dome area, for example, with the exception of the patient's head 15 are coated with a sound-insulating layer 101 which is about 40 mm thick and which is provided on its surface in turn with the whitest possible coat of paint which produces a diffuse reflection ($TiO_2$, $MgO_2$ etc. as a paint additive).

The light sources 17 may be light bulbs, flash lights, lasers etc. which project light against the underside of the flat screen 16 either directly or through preceding filters. The use of the dome 10, the cover 27, the flat screen 16 and the homogeneous coat of paint thereupon as well as other parts projecting into the interior of the dome 10 ensures that the light sources 17 produce a constant intensity of light throughout the entire field of vision without providing fixable contours for the patient. At the same time, one of the most essential tasks of the dome is to minimize undefined and undesirable ambient stimuli for the patient.

A separate invention is seen in the afore-described arrangement for stimulus application in itself.

Another optical stimulus generator and generator of audible semantic information is a double projection system 26 (FIGS. 4a, 4b) whose axes form an angle of approximately 60 to 90 degrees. The projection system includes wide-angle optical lenses (fisheye lenses) which permit projections of images up to angles of approx. 180 degrees. The projection system makes it possible to produce patterns or other pictorial information throughout the entire field of vision without any reference contours (e.g. borders). Stereo information can also be projected in the center in the area of overlap.

Two versions of the projection system 26 are possible: either the projection of normal slides or closed pattern rings which can be moved in at least two directions in the focal plane of the projector to thereby project moving patterns, or the projection is effected via a wide-angle lens by means of small colored cathode ray tubes of high luminance (brightness).

The distortion which occurs during wide-angle projection and which is modified due to the spherical projection screen formed by the dome 10 can be compensated for when projecting patterns according to the first variation by correspondingly distorting the patterns on the film. In the case of the second variation, this is done by controlling the cathode ray tubes corresponding to an image coordinate transformation.

Two loudspeakers 29 and 30 (8 Hz–20 kHz) located on opposing surfaces to the right and left of the head of the patient 15 along a transverse axis of the dome 10 are provided as the audible stimulus generators and generators for audible semantic information. The sound-insulating layer 101 is interrupted at these locations. It is also possible to provide more than two loudspeakers, 8 for instance, which are arranged in a distributed manner to encompass the patient's head. Such arrangements can be used to achieve stereophony or quadrophony directional effects and, under certain circumstances, with the aid of additional filters, distance effects etc.

The dome 10 is rotatably mounted in a pedestal 22 and can be raised upwardly at the one side by means of a cable 11, 12. The interior of the dome is ventilated by means of an axial blower or fan. The fresh air can enter the dome near the head of the patient 15.

The chair 24 is adapted to be tilted through a small angle (smaller than 15°) about the bearing 241. In this manner, the patient can be subjected to acceleration stimuli via a hydraulic servomotor (not shown). Slow rocking movements (with a sine-shaped curve) with a frequency of 0.2 to 0.25 Hz, for example, have an obvious soothing effect on the patient.

Furthermore, adjustable mechanical adaptation flanges 20 are provided on the chair 24 and are adapted to accommodate either physiological sensors or mechanical and electrical stimulus generators (see FIGS. 5–8). The sensors or stimulus generators are automatically connected to the appropriate leads 19 when they are snapped into their mounts. The leads 19 establish the connection between the patient 15 and the electronic preparation and adaptation equipment accommodated in the equipment console 18 which is designed as a cabinet. This electronic equipment fulfills the task of adapting the diverse measurement and signal levels of the sensors and generators to standard amplitudes (e.g. TTL levels etc.).

Removable inserts 281 and 282 are provided in the base plate 28 and make it possible for the therapist 13 to remain in direct contact with the patient being treated if these are very sensitive persons (familiarization). The choice of the arrangement of the chair 24 and the dome 10 such that the patient only partially projects into a closed space as exists in the interior of the dome 10 also serves to alleviate fear, anxiety and even claustrophobic reactions.

The therapist normally stands at a control panel 14 outside the dome 10 from where he is able to view the patient 15 through a small window 23.

The control panel 14 contains the electronic control equipment for the stimulus generators, i.e. the rhythm interval generator 151, the buffer memory 150, the control oscillator 153, the cassette recorder 155, the stimulus contour generator 252 and the tape memory 368. The therapy program is stored on a tape cassette which is inserted externally.

The light sources 17 are controlled by the stimulus contour generator 252. A defined rhythmic progression of the stimulus parameters brightness and color, for example, can be achieved in this manner. Likewise, the cathode ray tubes of the double projection system 26 are also controlled to produce certain images or the movement of the slides by the stimulus contour generator 252. The loudspeakers 29 and 30 are controlled by the stimulus contour generator so as to regulate the audible parameters of pitch and volume. In accordance with a general conception of the invention, the rhythm interval generator and the stimulus contour generator in the arrangement described in conjunction with FIG. 2 are thus equally suitable for producing music very generally and, in addition, for therapeutic use. Audible semantic information is supplied to the loudspeakers 29 and 30 from the tape memory 368. Furthermore, the stepping motor for moving the chair 24 and the mechanical and electrical stimulus generators to be mounted on the adaptation flanges are controlled by the stimulus contour generator.

In addition, when a number which can be determined by the therapist of physiological and technical parameters has exceeded the set limits, this is indicated on the control panel as well thus enabling the therapist to react quickly in particular in the event of unforeseen incidents.

Moreover, a keyboard (not shown) is located on the control panel 14 which can serve for manual program input in addition to the tape cassette. Furthermore, a remote control means 141 is also located on the control panel 14 which makes it possible for the therapist to control the most important functions of the console when he is inside in the interior of the dome, for example during the initial phase.

An easily accessible button (not shown) is provided on the right and left sides on the underside of the arm rest of the chair 24 which permits the patient to make a manual feedback to discontinue the stimulus treatment and to raise the dome 10 in case of nausea, anxiety, etc., to directly participate in the stimulus pattern sequence to achieve a desired effect, or to communicate a subjective feeling or state. In addition to the button, slide resistors (not shown) are also provided beneath the arm rests as well which not only permit manual yes/no information, but analogue manual information as well.

Figure 6:
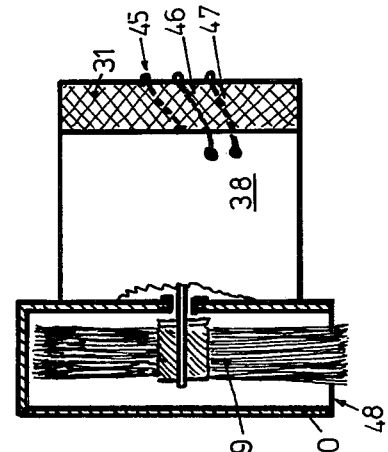

FIGS. 5, 6 and 7 show stimulus generators for applying mechanical and electric stimuli to selected body parts (e.g. locations with increased electrical conductivity).

FIG. 5 illustrates a stimulus generator for local punctiform or laminar stimuli comprising interchangeable contact elements 36, 37. The one contact element has the shape of a tip, while the other is provided with a spherical surface of large volume. A solenoid 34 with a hole in the center is provided to move the contact elements 36 and 37. The core aperture is lined with a sleeve 43 of a dielectric material. A ferromagnetic piston 33 is located in the interior of the sleeve 43. The contact elements 36 and 37 can be attached to one end of said piston. At the other end of the ferromagnetic piston 33 a spiral spring 35 is attached at one of its ends, while the other end is connected with an insertable mounting element 44 which insulates the sleeve 43 with respect to the solenoid. The solenoid includes a mounting flange 31 which can be connected to an adaptation flange 20 (FIG. 4). The contact elements are of metal or are metallized and may also be used as stimulus current electrodes, for which reason a lead 45 is provided which via the mounting element 44 establishes an electrical connection to the ferromagnetic piston 33 and thus to the contact element 36 or 37 attached thereto. Another possibility is to pass the lead 45 through and insulate it from the spring 35 and the piston 33 to a plug which establishes an electrical connection between the lead 45 and the contact element 36 or 37 when said contact element is attached to the piston. In this case, electrical insulation is provided between the piston 33 and the contact element 36 or 37. Two other leads 46,47 serve to supply current to the solenoid.

During operation the stimulus generator in FIG. 5 is disposed such that the contact element 36 or 37 is moved at an angle, preferably perpendicular to the skin surface, thus exerting a pressure stimulus which is provoked by movement of the tissue. If the stimulus is repeated more frequently than 5 times per second, this is termed a vibration stimulus and is differentiated from slow rhythmic massage or the application or occasional individual stimuli. The movement of the contact elements by corresponding excitation of the solenoid 34 is controlled by the stimulus contour generator 252 accommodated in the control console 17. Furthermore, rhythm can also be imparted to vibrations in the amplitude modulation procedure as well.

FIG. 6 illustrates a stimulus generator for stroke stimuli. An electromotor 38 causes a brush 39 to rotate with radial bristles and mounted on the shaft of the electromotor in a housing 40 with an opening 48. The housing opening 48 is selected such that the bristles project beyond the housing. The electromotor includes a mounting flange 31 adapted to be attached to an adaptation flange 20. The bristles of the brush 39 are of metal or are metallized and in turn can be used as an electrode. For this purpose, an electric lead 45 is provided which is connected with the bristles of the brush. The brush body and the shaft are electrically insulated with respect to the other parts of the stimulus generator. Two other electrical leads 46,47 serve to supply current for the electromotor 38.

For operation, the stimulus generator shown in FIG. 6 is positioned and mounted such that the brush axis extends substantially parallel to the skin surface. The brush is adapted to apply light surface stimuli without substantial pressure components which possess a strong afferent stimulus effect within the scope of reflex defense reactions. The electromotor 38 and thus the rotational speed of the brush 39 are again controlled by the stimulus contour generator 252 located in the control console 17. In addition, the stimulus generator shown in FIG. 6 can also be positioned such that it is raised and lowered substantially perpendicular to the skin surface, while being controlled by the stimulus contour generator 252, thereby permitting the force with which the brush acts against the skin to be varied rhythmically.

FIG. 7 illustrates a stimulus generator for circular massage stimuli. An electromotor 38 drives a rotation plate 41 which is secured to the shaft of said electromotor, which is positioned perpendicular thereto and to which a large contact element 42 with a spherical surface is attached at the rim. The electromotor again includes a mounting flange 31 intended to be connected to an adaptation flange 20. An electric lead 45 is again provided for establishing an electrical connection with the contact element 42 so that this can also be used as an electrode as well. The contact element, the rotation plate and the shaft are electrically insulated with respect to the other parts of the stimulus generator. Two other leads 46,47 serve to supply current to the electromotor 38.

For operation, the stimulus generator shown in FIG. 7 is positioned and mounted such that the axis of rotation extends substantially perpendicular to the skin surface. The stimulus is caused here by the circular movement of tissue. The electromotor 38 and thus the frequency of rotation of the contact element 42 is controlled by the stimulus contour generator 252 located in the control console 17.

FIG. 8a illustrates on a greatly enlarged scale a section of a flexible laminar electrode which can easily be manufactured in any desired size and configuration. Loose felt 53 is embedded between two plastic sheets 51 and 52 which are spaced apart from one another. The plastic sheet 52 includes spaced holes which are traversed by plastic filament bundles 54 penetrating into the felt 53. The filament bundles 54 are bent in a U-shaped configuration and respectively extend from outside the plastic sheet 52 through one of said holes into the felt 53, from there they continue back to the outside through an adjacent hole in said plastic sheet 52. The ends of the filament bundles form a carpet-like surface. In order to stiffen the filament bundle on the outer side of the plastic sheet 52, a reinforcement jacket 55 (FIG. 8b) is provided for each end of the bundle which encompasses the filament bundle and which also extends through the hole traversed by the associated end of the filament bundle into the area between the sheets 51 and 52.

The space between the sheets 51 and 52 communicates with a reservoir and equalizing container 56 for an electrolyte 16 with which the loose felt 53 is impregnated.

The spaces between the individual filaments of a filament bundle form capillary zones 57 (FIG. 8c) into which the electrolyte from the felt 53 penetrates. The action of the capillary zones ensures on the one hand that the ends of the filament bundles 54 are always adequately wetted with electrolytic liquid and they prevent on the other hand excess electrolytic liquid from escaping.

Spacing elements 58 are provided between the sheet 51 and the felt 53 on the side of the plastic sheet 51 through which said filament bundles do not pass. These spacing elements can be integral with, welded to or glued to the sheet and form an empty space between the felt 53 and the sheet 51, thus preventing the electrolytic liquid from being squeezed out of the felt when an electrode with a small radius of curvature is applied to a body part. On the side of the sheet 52 through which the filament bundles 54 pass, the felt is spaced from the sheet 52 by the filament bundles 54 themselves which have their reinforcement jackets 55 anchored in the sheet 52.

A metal conductor 59 is embedded in the felt 53 to establish contact.

The potential applied to the electrode is controlled by the stimulus contour generator 252 located in the control console 17. An embodiment of the electrode featuring a large surface area is used to influence nerve potentials. The voltage amounts to 30 to 60 volts and the current density amounts to 0.5 to 1 mA/sq.cm. of body surface.

An embodiment of the electrode featuring a small surface area amounting from 4 to 8 sq.cm. is used to activate specific groups of muscles with the aid of stimulus current pulses produced by the stimulus contour generator 252.

I claim:

1. A device for exposing a body to stimuli and for detecting the response of said body to stimuli, comprising:
   first means for producing a plurality of series of first signals, the values of said first signals in each series representing time intervals,
   second means for producing signals corresponding with basic time units, said first means using said basic time units to determine the lengths of the intervals in each series,
   memory means for storing said first signal values for each series,
   stimulus contour signal generator means having input and output means and being operative to recall the values stored in said memory, to count up to the respectively recalled values and to assign a value to each basic unit so that a series of these values taken in succession defines the contour of the stimuli within each of said time intervals,
   stimulus generator means for producing said respective body responsive stimuli, and
   means for coupling said output means of said stimulus contour generator means to said stimulus generator means, respectively.

2. Apparatus for producing body responsive stimuli, comprising:
   an interval generator for producing signals which have values that define the duration of intervals for individual sequences of intervals,
   a stimulus signal contour generator for producing time-varying stimulus signal contours within the respective defined intervals,
   a plurality of stimulus generators, respectively responsive to stimulus signal contours in the respective sequences by producing body responsive stimuli,
   means for coupling the signal sequences from said contour generator to the respective stimulus generators,
   means for detecting various reactions of a body to respective stimuli,
   means for producing feedback signals representative of reactions, and
   means for coupling said feedback signals to said interval generator for said generator to respond by altering said intervals in correspondence with the characteristic of the feedback signal.

3. Apparatus for producing body responsive stimuli, comprising:
   an interval generator for producing signals which have values that define the duration of intervals for individual sequences of intervals,
   a stimulus signal contour generator for producing time-varying stimulus signal contours within the respective defined intervals,
   a plurality of stimulus generators, respectively responsive to stimulus signal contours in the respective sequences by producing body responsive stimuli,
   means for coupling the signal sequences from said contour generator to the respective stimulus generators,
   means for detecting various reactions of a body to respective stimuli,
   means for producing feedback signals representative of reactions, and
   means for coupling said feedback signals to said stimulus signal contour generator for said contour generator to respond by altering the contour of said stimulus signal in correspondence with the characteristics of said feedback signal.

4. A device according to claim 2 or 3 wherein said interval generator (151) is operative to represent said intervals as pluralities of basic units, and means (153) for controlling the length of time of said basic units, said stimulus signal contour generator including means for counting the numbers of basic units in the intervals, respectively, and for responding to the counts by adjusting the durations of the stimulus signals that comprise the signal contours to fit the contours within the intervals.

5. A device according to claim 4, including a buffer memory (150) for intermediate storage of the said pluralities of basic units, which represent the respective intervals, said buffer memory having input means coupled to said interval generator and output means coupled to said stimulus contour generator to enable said contour generator to use one set of said interval values from said buffer memory while another set is being generated by said interval generator.

6. A device according to claim 2 or 3 including an opaque, sound insulating enclosure (10) for enclosing at least a part of a patient and said stimulus generators simultaneously, means for observing a patient through the enclosure, means for pivotally supporting the enclosure, and means for swinging the enclosure on said pivot.

7. A device as in claim 2 or 3 including means for supporting a patient for being subjected to examination, said stimulus generators including at least one light source and at least one sound source disposed in proximity to said patient supporting means, hollow dome means for enclosing said patient supporting means and said stimulus generators simultaneously for isolating said patient from ambient sound and light, screen means disposed in the path of light emanating from said light source to the interior of said dome means, the interior of said dome means and the surfaces of said screen means and other surfaces of objects disposed in said dome means which are capable of reflecting light having a coating of white diffusely reflecting material on them.

* * * * *